United States Patent
Shofner

(10) Patent No.: US 6,300,631 B1
(45) Date of Patent: Oct. 9, 2001

(54) METHOD OF THINNING AN ELECTRON TRANSPARENT THIN FILM MEMBRANE ON A TEM GRID USING A FOCUSED ION BEAM

(75) Inventor: Terri L. Shofner, Casselberry, FL (US)

(73) Assignee: Lucent Technologies Inc., Murray Hill, NJ (US)

( * ) Notice: Subject to any disclaimer, the term of this patent is extended or adjusted under 35 U.S.C. 154(b) by 0 days.

(21) Appl. No.: 09/414,221

(22) Filed: Oct. 7, 1999

(51) Int. Cl.[7] ............ G01N 23/00; G21K 7/00; G21K 5/10
(52) U.S. Cl. ............ 250/311; 250/310; 250/442.11; 250/307
(58) Field of Search ............ 250/311, 307

(56) References Cited

U.S. PATENT DOCUMENTS

| | | | |
|---|---|---|---|
| 5,270,552 | * 12/1993 | Ohnishi et al. | 250/307 |
| 5,783,830 | 7/1998 | Hirose et al. | 250/492.21 |
| 5,799,104 | 8/1998 | Nakamura et al. | 382/144 |
| 5,894,058 | 4/1999 | Hatakeyama et al. | 430/313 |
| 5,986,264 | * 11/1999 | Grunewald | 250/310 |

OTHER PUBLICATIONS

Coating Grids and custom coating service from spi, SPI Supplies, http:// www.2spi.com.*

* cited by examiner

Primary Examiner—Jack Berman
Assistant Examiner—Kalimah Fernandez
(74) Attorney, Agent, or Firm—Allen, Dyer, Doppelt, Milbrath & Gilchrist, P.A.

(57) ABSTRACT

A method of thinning a cut electron transparent membrane used in transmission electron microscopy is disclosed. An electron transparent thin film membrane is cut from a sample that is positioned within a focused ion beam device by focusing an ion beam in a predetermined direction onto the sample to mill the sample and cut the transparent thin film membrane from the sample. The membrane is mounted onto a transmission electron microscope grid having a mesh surface and carbon coating. It is mounted in a vertical orientation onto a support stage of a focused ion beam device such that the membrane is mounted vertically and parallel with the incident focused ion beam produced by the focused ion beam device. The support stage is tilted a predetermined amount to orient the membrane at an angle incident to the focused ion beam. The ion beam is focused at a glancing angle into a predetermined portion of the membrane for thinning the membrane by cutting a thin portion from the membrane.

21 Claims, 7 Drawing Sheets

METHOD OF THINNING AN ELECTRON TRANSPARENT THIN FILM MEMBRANE ON A TEM GRID USING A FOCUSED ION BEAM

FIELD OF THE INVENTION

This invention relates to a method of focused ion beam milling, and more particularly, this invention relates to a method of focused ion beam milling a cut electron transparent membrane used in transmission electron microscopy.

BACKGROUND OF THE INVENTION

Membranes used in transmission electron microscopy (TEM) are prepared by a focused ion beam (FIB) that are routinely used to prepare site specific TEM specimens of semiconductor devices. A site is prepared for milling with a focused ion beam and trenches are milled parallel to a 1–2 millimeter thick platinum (Pt) film that has been deposited on the surface. When the film is approximately 300 nanometers thick, the focused ion beam cuts are made to partially detach the section from the wafer. The wafer is tilted to 60°, exposing the base and sides of the film. The focused ion beam cuts are then made at the base and sides to produce a "flag on a pole" configuration. The final "release" cuts are usually made at a 0° tilt.

The wafer is usually removed from the focused ion beam and placed under an optical microscope having a long working distance objective lense and a micromanipulator with coarse and fine adjustments. A glass pipette is usually attached to the micromanipulator to remove the TEM film from the wafer. The pipette is usually positioned over the film and lowered to contact it. The electrostatic forces attract the film to the tip of the pipette, which is then raised from the wafer surface. The microscope stage is then moved to bring a TEM grid into view. The pipette with the dangling film is then lowered and the TEM film dropped on the grid.

A major drawback of this process is that once a sample is mounted on the TEM grid, it cannot be further thinned if the membrane is too thick for electron transmission. Thus, a second sample must be prepared, and if the sample is prepared from a specific site on the sample, such as the semiconductor, the specimen is lost. Some uses of an argon mill to further thin the mounted sample have been attempted, but the carbon film typically used on the grid is destroyed and the sample is then lost in the vacuum because it cannot be retained on the grid.

SUMMARY OF THE INVENTION

It is therefore an object of the present invention to provide a method of thinning a cut electron transparent membrane used in transmission electron microscopy that is mounted on a transmission electron microscope grid.

The method of the present invention allows the thinning of a cut electron transparent membrane used in transmission electron microscopy when it is mounted on the transmission electron microscope grid. The method comprises the step of cutting an electron transparent thin film membrane from a sample that is positioned within a focused ion beam device by focusing an ion beam in predetermined directions onto the sample to mill the sample and cut the electron transparent thin film membrane from the sample. The thin film membrane is lifted-out from the sample and then mounted onto a transmission electron microscope grid having a mesh surface and carbon coating. This grid is then mounted in a vertical orientation onto a support stage of a focused ion beam device such that the vertical orientation of the membrane is parallel with the incident focused ion beam produced by the focused ion beam device. The support stage is tilted a predetermined amount to orient the membrane at an angle incident to the focused ion beam. The focused ion beam is then focused at a glancing angle into a predetermined portion of the membrane for thinning the membrane by cutting a thin portion from the membrane.

In one aspect of the present invention, the method comprises the step of tilting the support stage such that the focused ion beam is about 5° to about 15° normal with a vertical orientation of the thin film membrane. The membrane can be mounted on the grid with the carbon coating face down opposite the membrane. The method can also comprise the step of mounting the membrane on a transmission electron microscope grid having a copper mesh surface. This grid can comprise a 400 mesh transmission electron microscope grid.

In still another aspect of the present invention, the method can comprise the step of focusing an ion beam at a lower voltage and current during the thinning step than the voltage and current used when milling the membranes from the sample, such that only the carbon coating adjacent the area that is milled is destroyed to aid in retaining the membrane to the transmission electron microscope grid. The step of milling the membrane in the sample can be at a current of about one microampere. The step of thinning the membrane after removal from the sample can be at a current of about 10 to about 100 picoamperes.

The method can also comprise the step of milling the membrane in the sample to a thickness of about 0.1 to about 0.2 micrometer thickness. The step of thinning the membrane can be about removing 100 nanometers of material. The step of lifting-out the electron transparent thin film membrane can comprise the step of lifting-out from the sample with a charged glass rod.

BRIEF DESCRIPTION OF THE DRAWINGS

Other objects, features and advantages of the present invention will become apparent from the detailed description of the invention which follows, when considered in light of the accompanying drawings in which.

DETAILED DESCRIPTION OF THE PREFERRED EMBODIMENTS

The present invention is advantageous because it now allows an electron transparent thin film membrane used for transmission electron microscopy (TEM) to be routinely prepared by the focused ion beam (FIB) device using a lift-out method and be thinned in the FIB device in a novel and unobvious way such that the integrity of the grid coating can be maintained, while directing the beam to a specific area where thinning is required. This novel and unobvious process saves the time of preparing a membrane a second time and allows the reprocessing of unique membranes that would otherwise be destroyed. The present invention also provides a simple method of reintroducing the membrane to the FIB and allowing low damage, site specific thinning.

For purposes of description, a focused ion beam device is first described followed by a method for focus ion beam milling and micromanipulation lift-out for site specific cross-section TEM specimen preparation of membranes that can later be placed in the FIB and thinned.

Figure 1:
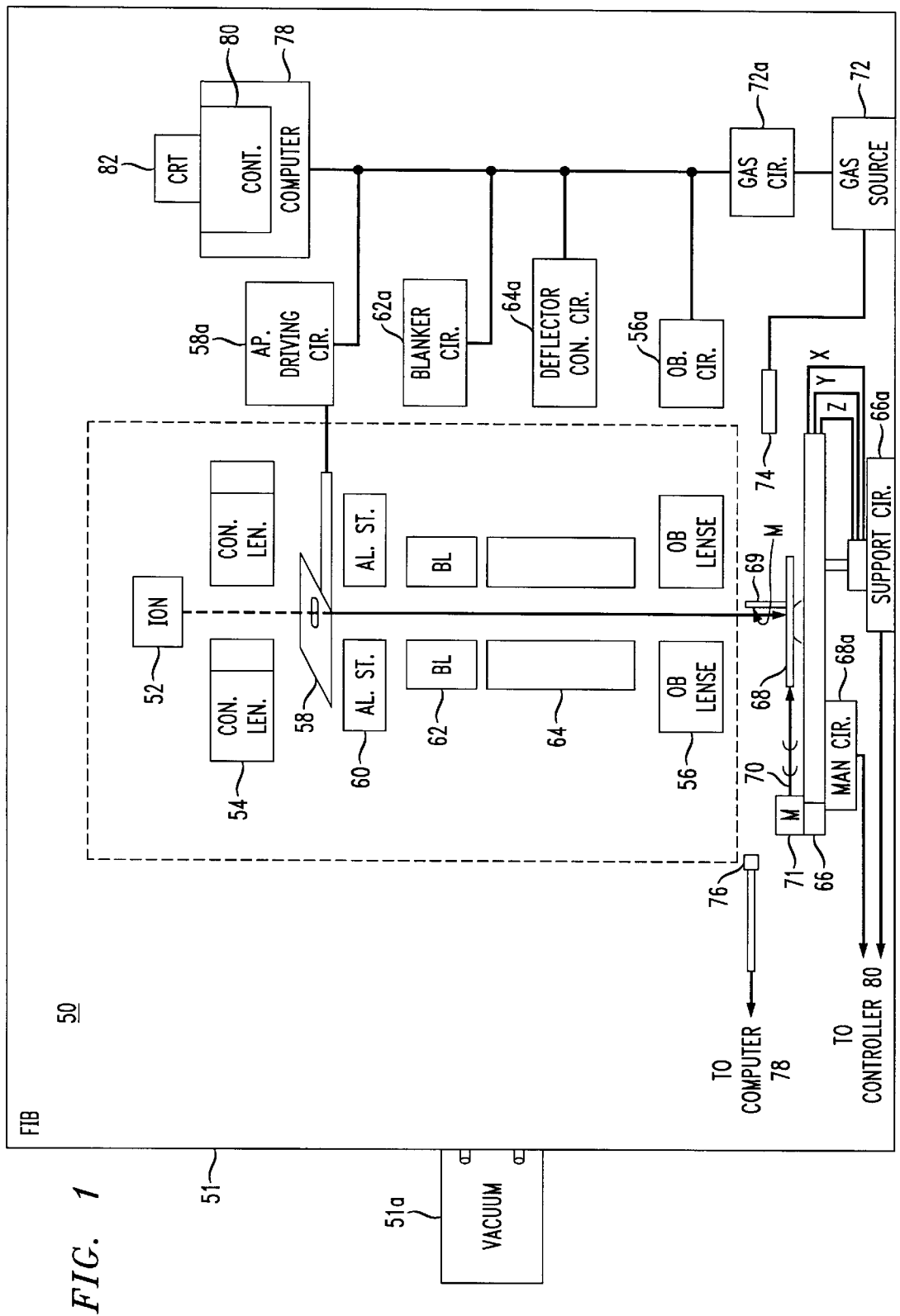
FIG. 1 is a schematic diagram of a focused ion beam (FIB) device and shows its use in milling a semiconductor device for forming a thin film membrane.

As shown in FIG. 1, a focused ion beam device 50 (FIB) is illustrated. The FIB device 50 and associated components and peripherals, such as mounts, are contained in a large FIB vacuum chamber 51, where vacuum is drawn by vacuum pump 51a. A focused ion beam spot size can vary from micrometers to as finite as 5 nanometers, or 50 angstroms. The FIB device 50 can make precise drills and cuts (e.g., milling cuts).

The focused ion beam device 50 typically includes a liquid metal ion source 52 from which ions can be emitted. Gallium ions or other suitable ions known to those skilled in the art can be emitted. The ion beam is focused on a specimen through a condenser lens 54 and a spaced objective lens 56. A selectable aperture 58 is positioned under the condenser lens 54 and liquid metal ion source 52. An aligner-stigmator 60, blanker 62 and deflector 64 can be arranged between the two lenses. The selectable aperture 58 is connected to an aperture driving circuit 58a. The blanker 62 is connected to a blanking amplifier circuit 62a. The deflector 64 can be connected to a deflection control circuit 64a. These types of circuits are known to those skilled in the art.

A support 66 mounts semiconductor devices or other sample or grids, and is mounted for movement in at least three axes (X, Y and Z) directions, and often by appropriate control through various other axes. A manipulator 68 is fixed to a rotary shaft 70 and driven by motor 71 mounted on the support 66. The manipulator 68 and X, Y, Z movable support 66, also referred to in this example as a support stage, allows movement of the grid in directions other than the X, Y and Z axis. A TEM grid 69 is illustrated in dotted line configuration and mounted vertically on the support stage 68, i.e., manipulator, and having a membrane M mounted thereon. A gas such as $WCO_6$ can be produced from a gas source 72 and inserted by nozzle 74 into the area where the semiconductor device is to be irradiated. The gas nozzle 74 can be positioned adjacent the semiconductor device that is positioned on the support 66.

Additionally, the FIB device 50 could include a secondary electron detector 76 that allows secondary electrons produced from the surface of the semiconductor device to be detected. The generated signal could be converted from an analog signal into a digital signal and supplied to a computer 78 that works in synchronism with the controller 80 that controls the deflection of the focused ion beam. Thus, an image can be formed by a scanning ion microscope and displayed on a cathode ray tube (CRT) 82.

The manipulator 68 is controlled by a manipulator control circuit 68a to allow manipulation in rotative directions as compared to the axes (X, Y and Z) controlled by a support circuit 66a. The controller 80 can control the aperture driving circuit 58a through a system bus 84 and select desired aperture from the selectable aperture 58. The computer 78 and associated controller 80 control the deflection control circuit 64, manipulator control circuit 68a, the support control circuit 66a, the gas source control circuit 72a and other circuits. All portions of the device 50 can be controlled, including the power source 56 for the lenses. These components are mounted in the vacuum chamber 51 to allow a gas free environment.

A second focused ion beam device could also be mounted within the chamber 51 to allow a focused ion beam to be emitted at a different direction. However, typically, only one focused ion beam device is required. Any semiconductor device or sample is moved and rotated as necessary.

As noted before, one of the most valuable areas of interaction has been preparation of specimens for transmission electron microscopy (TEM). The first TEM specimens that were prepared required traditional mechanical thinning prior to FIB final thinning. The final thinning steps using the FIB resulted in TEM transparent membranes that not only could be obtained from a very specific site, but also provided a large area of uniform thickness so that information such as the presence of localized internal stress around features could be detected.

For some classes of materials, however, it is difficult or impossible to perform the initial mechanical thinning. Another disadvantage to the conventional FIB method is that large cut trenches produce walls of material on either side of the thin membrane which results in limited tilting capabilities (e.g., ±5°) during TEM analysis. This lead to the concept of a "lift-out" method where the electron transparent membrane may be removed from the bulk specimen. This more advantageous method uses commercially available hardware to remove samples for TEM analysis from virtually any material without prior preparation.

The advantage to the lift-out technique is that virtually no initial specimen preparation is needed prior to FIB thinning. This process is described below relative to the preparation of an FIB TEM specimen using the cross-section of an integrated circuit, as an example.

Figure 2A:
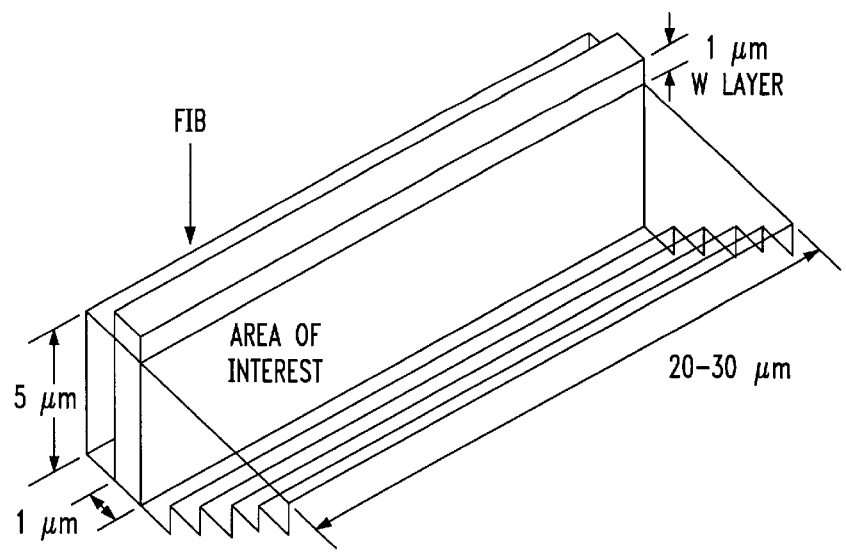
FIGS. 2A–2C are drawings illustrating the milling steps used in the focused ion beam device for milling a thin film transparent membrane.
Figure 2B:
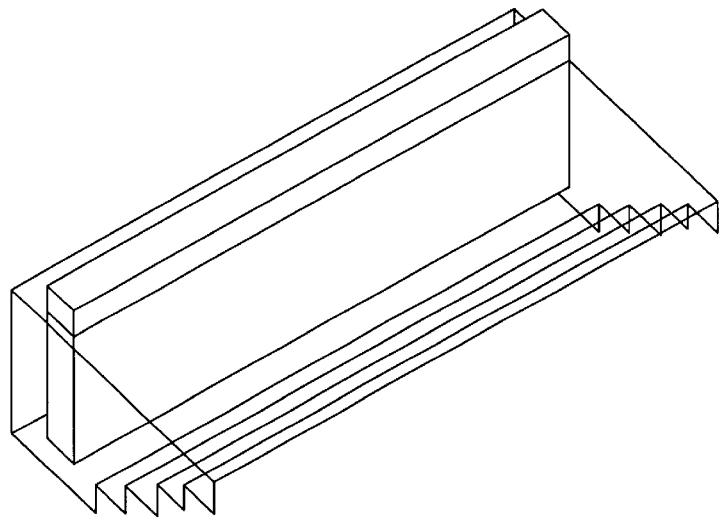
Figure 2C:
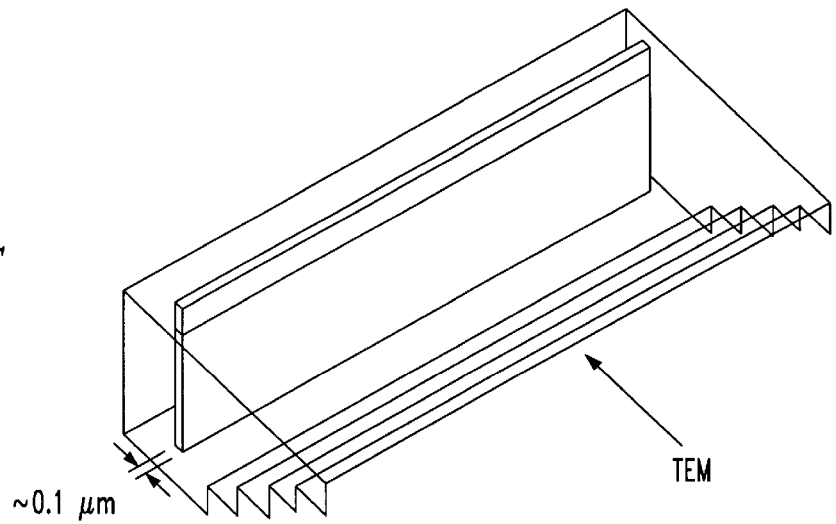

A schematic diagram of the important aspects of the technique is illustrated in FIGS. 2A–2C and the individual steps are shown in the scanning electron microscopy (SEM) images in FIGS. 3A–3F. Sample membrane preparation was performed on an FEI FIB 611 workstation. SEM images were obtained from a Hitachi S4100 operating at 6 kV, and TEM analysis was performed on a Philips EM430 operating at 300 kV, equipment known to known those skilled in the art.

Figure 3A:
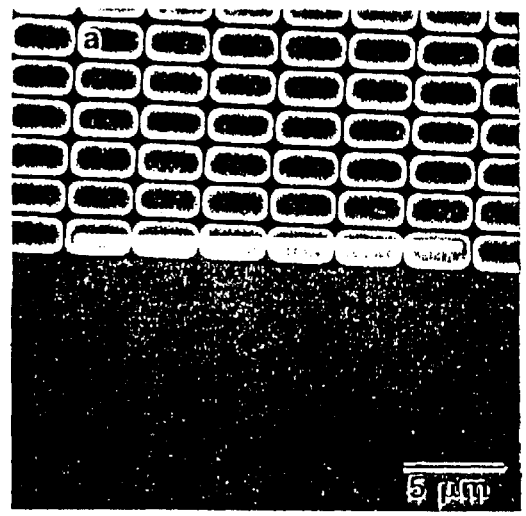
FIGS. 3A–3F are scanning electron microscope images of the individual sequences for the focused ion beam cutting of a cross-section transmission electron microscope thin film membrane.
Figure 3B:
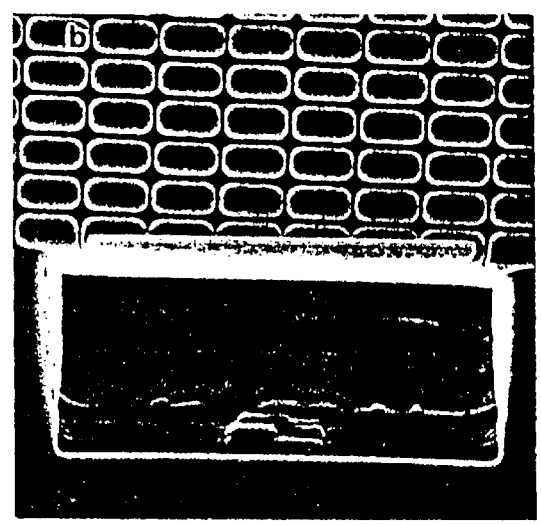

A desired sample is placed into the FIB chamber 50 and a suitable region is identified for cross-section specimen preparation. The area to be cross-sectioned is covered with a ~0.5 $\mu$m long×1 $\mu$m high protective layer (e.g., W or Pt) which prevents spurious sputtering of the top surface of the specimen and outlines the area of interest (FIGS. 2A and 3A). This metal deposition is accomplished by local decomposition of a gas by the focused ion beam (i.e., ion assisted chemical vapor deposition). Next a "stair step" trench of total dimension of approximately 5 $\mu$m wide by 30 $\mu$m long×5 $\mu$m deep (at the deepest step) is sputtered from one side, designated the front of the area of interest (FIGS. 2A and 3B). The stair step trench serves two purposes: (i) it enables the sputtered front surface of the specimen to be imaged upon tilting, and (ii) it saves half the time that would be required to sputter a rectangular trench. The stair step trench can be produced by using the software inherent to the instrument.

Figure 3C:
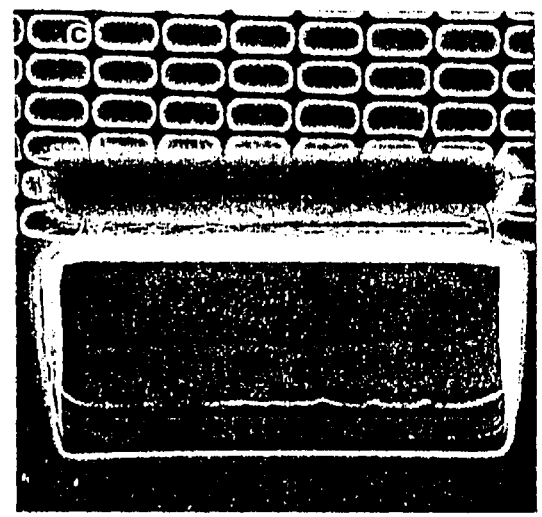
Figure 3D:
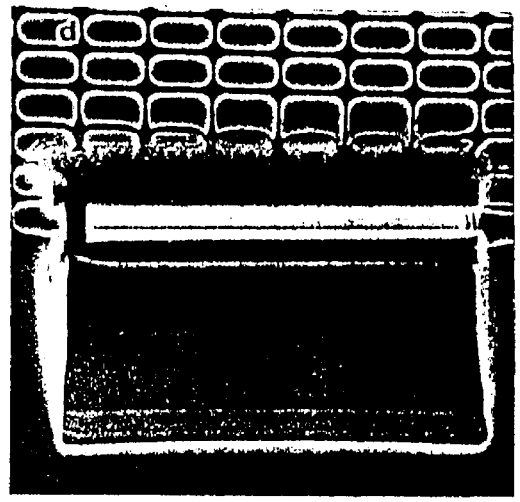
Figure 3E:
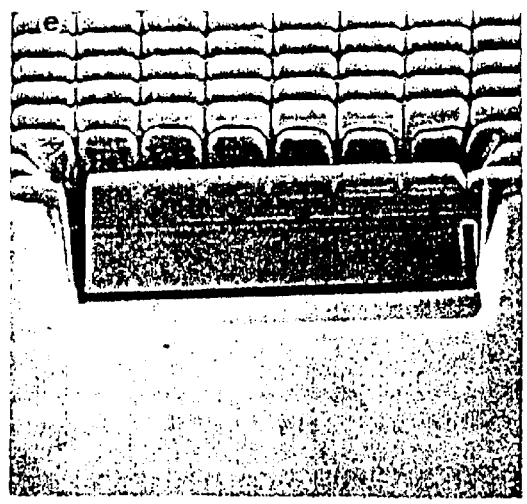
Figure 3F:
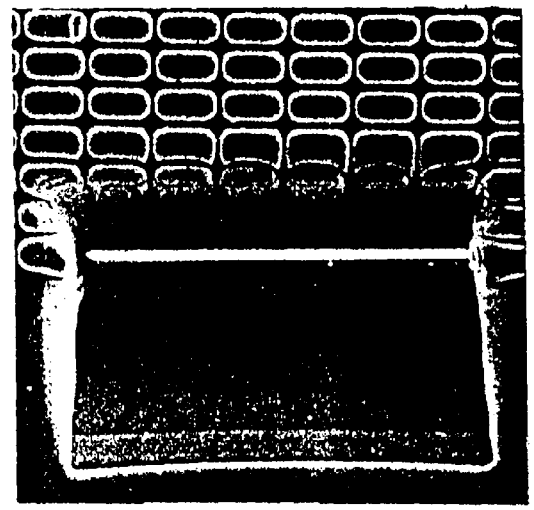

A small rectangular sized trench of approximate dimensions 2 µm wide×30 µm long 5 µm deep is then sputtered from the opposite side (or "back") of the specimen (FIGS. 2A, 3C). The specimen is further thinned to ~1 µm from the front and back and the left side is cut through (FIG. 3D). The sample os tilted approximately 50 degrees to reveal the front surface of the sputtered specimen. To prepare an isolated electron transparent membrane, the bottom and part of the right edge of the specimen are cut free (FIGS. 2B, 3E). The specimen is tilted back to its original position (zero degrees or normal incidence to the beam) and thinned to electron transparency (~0.1 µm=100 nm thick, see for example FIGS. 2C and 3F). The right edge of the specimen is cut completely free (FIG. 2C) and the specimen is ready to be removed from the FIB and micromanipulated to a copper grid 40. It should be noted that the trenches and rough FIB cuts are performed using a large high current ion beam on the order of 1 µA, while the final thinning is performed with a low current (tens of pA) ion beam.

Figure 4:
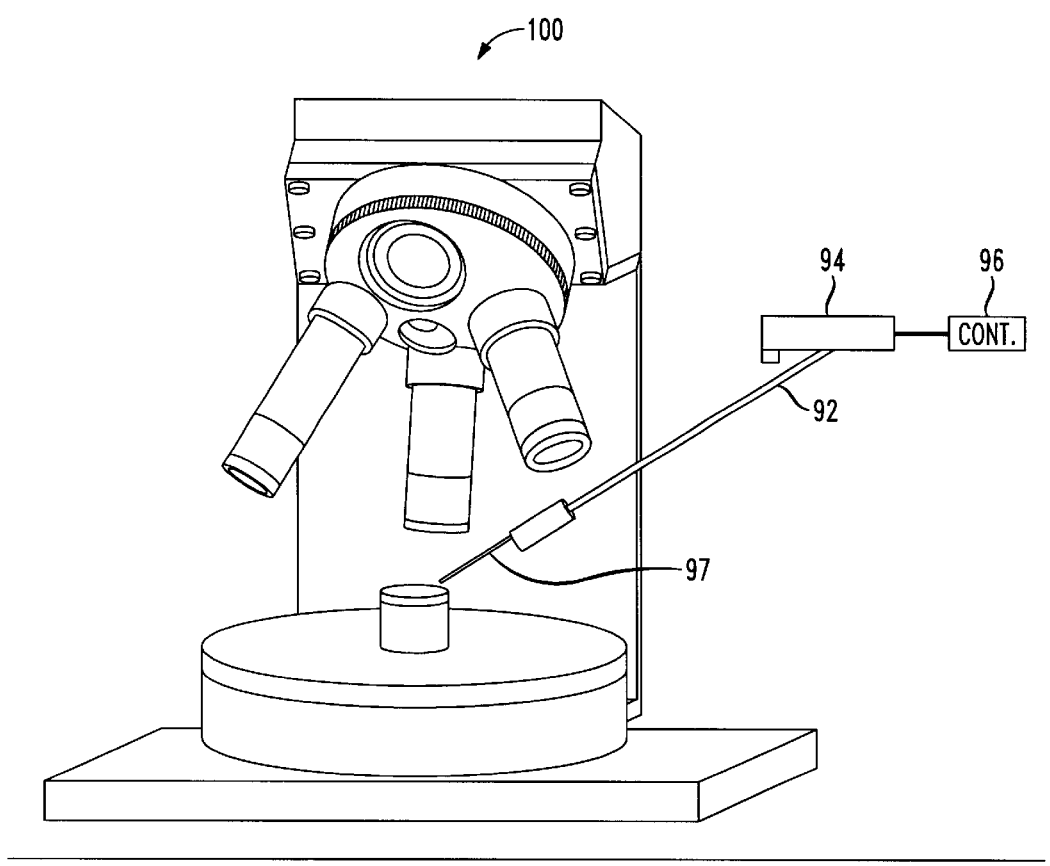
FIG. 4 is an image illustrating a bulk sample positioned on a light optical microscope stage that is ready for micromanipulation and lift-out.
Figure 5:
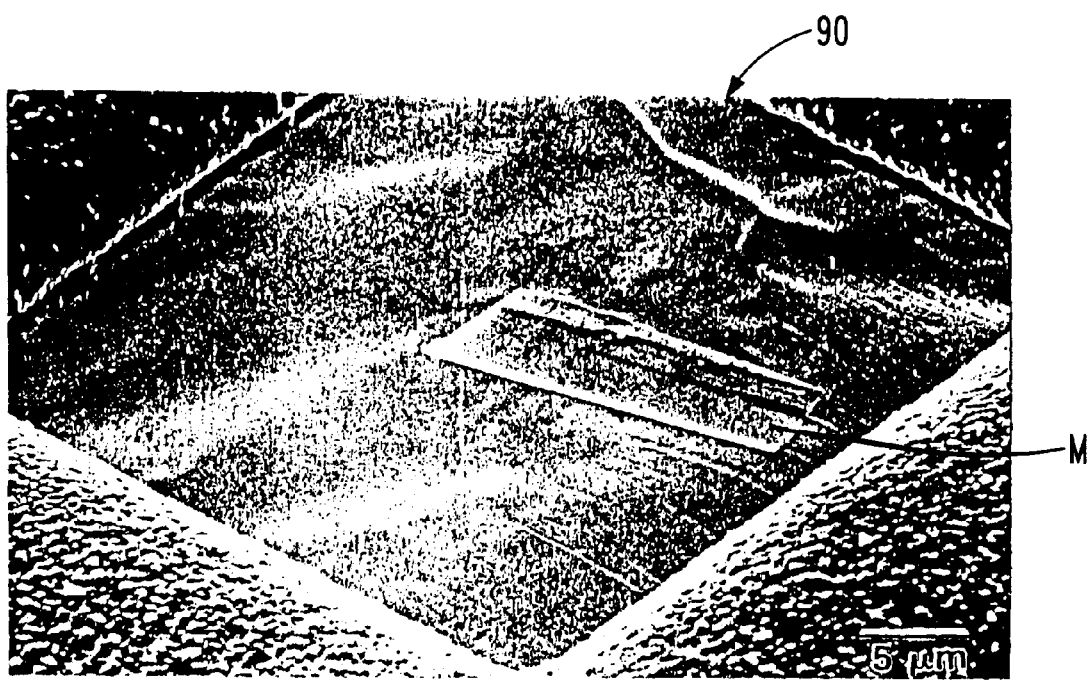
FIG. 5 is a scanning electron microscope image of a transmission electron microscope lift-out specimen positioned on a copper transmission electron microscope grid.

After the TEM specimen has been produced, the specimen is removed from the FIB specimen chamber and micromanipulated onto a formvar (or carbon) coated copper 400 mesh TEM grid 90, such as the type shown in FIG. 5. In one technique, a glass rod 92 is pulled to a sharp point and attached to the hydraulic arm of a micromanipulator 94 and controller 96. Using a light optical microscope 100, the glass tip of a glass rod 97 is lowered to the FIB prepared TEM specimen (see FIG. 4) and the specimen is plucked out of the cut trenches. The TEM specimen adheres to the glass rod 97 by electrostatic attraction. The sample holder is replaced by a carbon coated copper mesh grid, carbon film side down, and the glass rod/specimen assembly is lowered to the grid. The glass rod is then used to place the specimen onto the grid. The TEM specimen formed as a membrane M is flat and secure on the film when its front surface reflects brightly as observed through the light optical microscope. An SEM image of one TEM membrane mounted on a copper grid is shown in FIG. 5. The membrane produced is extremely rugged and remains on the grid during transport and vacuum pump-down in the TEM. More importantly, the entire specimen preparation process from insertion into the FIB to insertion into the TEM may take a total time of only about 3–5 hours.

The FIB lift-out technique as described is an excellent tool for performing TEM for quality control, failure analysis, and research and development in the microelectronics industry. In addition, this technique is also viable for applications in other materials systems. The specimens usually are devoid of ion milling damage, such as ion induced dislocation loops.

Figure 6:
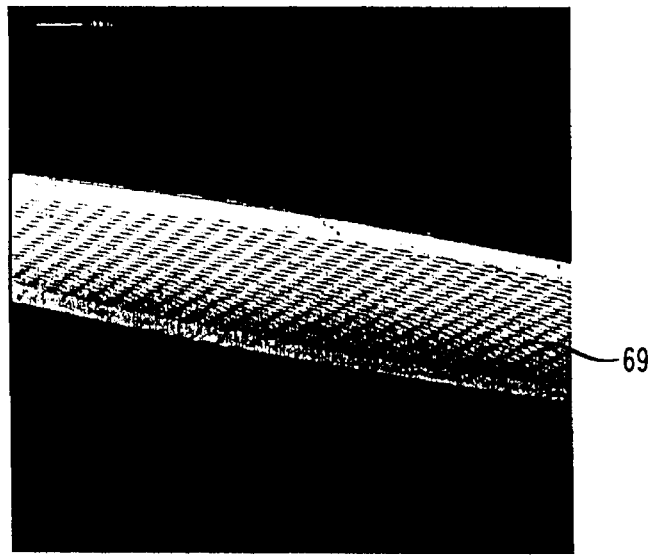
FIG. 6 is an image of a transmission electron microscope grid with a transparent membrane.
Figure 7:
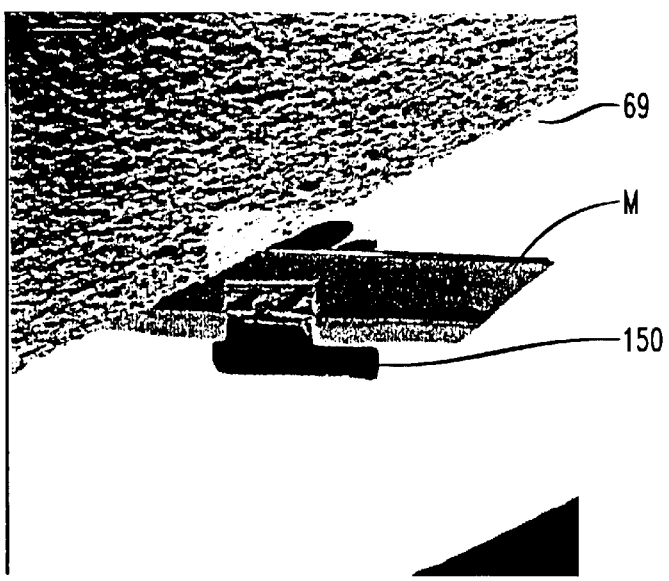
FIG. 7 is an enlarged image of the area of interest on the transparent membrane that can be thinned at low beam energy.

As shown in FIGS. 1 and 6, the TEM grid 67 is mounted vertically onto the support stage 66, 68. The membrane M is thus mounted vertically and is parallel with the incident focused ion beam produced by the focused ion beam device. The support stage 66, 68 is then tilted a predetermined amount to orient the membrane M at an angle incident to the focused ion beam. Thus, the ion beam can be focused at a glancing angle into a predetermined portion of the membrane for thinning the membrane by cutting a thin portion from the membrane. Typically, the support stage can be tilted such that the focused ion beam is about 5° to about 15° normal to the vertical orientation of the thin film membrane. Typically during the thinning step, about 100 nanometers of material is removed. The low beam voltage and current is used during the thinning process and is typically about 10 to about 100 picoamperes. The carbon backing 150 typically is only destroyed near the area being milled, leaving the balance of the carbon to hold the membrane securely in the TEM vacuum, such as shown in FIG. 7. Thus, a sample does not have to be prepared a second time if further milling is required. The grid could be held by an SEM clamp or other means known to those skilled in the art. The center of the circular grid can typically include an hour glass shaped receiver area to help in finding the center. The membrane would be mounted in that area to locate quickly.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that the modifications and embodiments are intended to be included within the scope of the dependent claims.

That which is claimed is:

1. A method of thinning a cut electron transparent membrane used in transmission electron microscopy comprising the steps of:
    cutting an electron transparent thin film membrane from a sample that is positioned within a focused ion beam device by focusing an ion beam in predetermined directions onto the sample to mill the Sample and cut the electron transparent thin film membrane from the sample;
    lifting-out the cut electron transparent thin film membrane from the Sample;
    mounting the membrane after it has been lifted-out from the sample onto a transmission electron microscope grid having a mesh surface and carbon coating;
    mounting the transmission electron microscope grid in a vertical orientation onto a support stage of a focused ion beam device such that the membrane is mounted vertically and parallel with the incident focused ion beam produced by the focused ion beam device;
    tilting the Support stage about 5 degrees to about 15 degrees to orient the membrane at an angle incident to the focused ion beam such that said focused ion beam will not strike said transmission electron grid; and
    focusing the ion beam at the glancing angle of about 5 degrees to about 15 degrees into a predetermined portion of the membrane for thinning the membrane by cutting a thin portion from the membrane.

2. A method according to claim 1, and further comprising the step of mounting the membrane on the grid with the carbon coating face down opposite the membrane.

3. A method according to claim 1, and further comprising the step of mounting the membrane on a transmission electron microscope grid having a copper mesh surface.

4. A method according to claim 1, wherein the grid comprises a 400 mesh transmission electron microscope grid.

5. A method according to claim 1, and further comprising the step of focusing an ion beam at a lower voltage and current during the thinning step than the voltage and current used when milling the membrane from the sample such that only the carbon coating adjacent the area that is milled is destroyed to aid in retaining the membrane to the transmission electron microscope grid.

6. A method according to claim 5, and further comprising the step of milling the membrane in the sample at a current of 1 micro ampere.

7. A method according to claim 5, and further comprising the step of thinning the membrane after removal from the sample at a current of about 10 to about 100 picoamperes.

8. A method according to claim 1, and further comprising the step of milling the membrane in the sample to a thickness of about 0.1 to about 0.2 micrometer thickness.

9. A method according to claim 1, and further comprising the step of thinning the membrane by removing about 100 nanometers.

10. A method according to claim 1, and further comprising the step of lifting-out the electron transparent thin film membrane from the sample with a charged glass rod.

11. A method of thinning a cut electron transparent membrane used in transmission electron microscopy comprising the steps of:
   mounting an electron transparent thin film membrane onto a transmission electron microscope grid having a mesh surface carbon coating;
   mounting the transmission electron microscope grid in a vertical orientation onto a support stage of a focused ion beam device such that the membrane is vertically oriented parallel with the incident focused ion beam produced by the focused ion beam device;
   tilting the Support stage about 5 degrees to about 15 degrees to orient the membrane at an angle incident to the focused ion beam such that said focused ion beam will not strike said transmission electron grid; and
   focusing the ion beam at the glancing angle of about 5 degrees to about 15 degrees to a predetermined portion of the membrance for thinning the membrance by cutting a thin portion from the membrane.

12. A method according to claim 11, and further comprising the step of mounting the membrane on the grid with the carbon coating face down opposite the membrane.

13. A method according to claim 11, and further comprising the step of mounting the membrane on a transmission electron microscope grid having a copper mesh surface.

14. A method according to claim 11, wherein the grid comprises a 400 mesh transmission electron microscope grid.

15. A method according to claim 11, and further comprising the step of cutting the membrane from a sample by focusing an ion beam on the sample in a predetermined milling directions.

16. A method according to claim 15, and further comprising the step of focusing an ion beam at a lower voltage and current during the thinning step than the voltage and current used when milling the membrane from the sample such that only the carbon coating adjacent the area that is milled is destroyed to aid in retaining the membrane to the transmission electron microscope grid.

17. A method according to claim 16, and further comprising the step of milling the membrane in the sample at a current of about 1 micro ampere.

18. A method according to claim 16, and further comprising the step of thinning the membrane after removal from the sample at a current of about 10 to about 100 picoamperes.

19. A method according to claim 15, and further comprising the step of milling the membrane in the sample to about 0.1 to about 0.2 micrometer thickness.

20. A method according to claim 15, and further comprising the step of lifting-out the electron transparent thin film membrane from the sample after milling with a charged glass rod.

21. A method according to claim 15, and further comprising the step of thinning the membrane by removing about 100 nanometers.

* * * * *